US010780158B2

(12) United States Patent
Plemper et al.

(10) Patent No.: US 10,780,158 B2
(45) Date of Patent: Sep. 22, 2020

(54) TUNABLE VACCINE PLATFORM AGAINST PATHOGENS OF THE PARAMYXOVIRUS FAMILY

(71) Applicant: GEORGIA STATE UNIVERSITY RESEACH FOUNDATION, INC., Atlanta, GA (US)

(72) Inventors: Richard Plemper, Decatur, GA (US); Veronika von Messling, Langen (DE)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/776,703

(22) PCT Filed: Nov. 16, 2016

(86) PCT No.: PCT/US2016/062324
§ 371 (c)(1),
(2) Date: May 16, 2018

(87) PCT Pub. No.: WO2017/087550
PCT Pub. Date: May 26, 2017

(65) Prior Publication Data
US 2018/0326046 A1   Nov. 15, 2018

Related U.S. Application Data

(60) Provisional application No. 62/255,711, filed on Nov. 16, 2015.

(51) Int. Cl.
| *A61K 39/175* | (2006.01) |
| *C07K 14/005* | (2006.01) |
| *C12N 7/00* | (2006.01) |
| *A61K 39/12* | (2006.01) |
| *A61K 39/00* | (2006.01) |
| *A61K 39/155* | (2006.01) |

(52) U.S. Cl.
CPC ............ *A61K 39/175* (2013.01); *A61K 39/00* (2013.01); *A61K 39/12* (2013.01); *A61K 39/155* (2013.01); *C07K 14/005* (2013.01); *C12N 7/00* (2013.01); *A61K 2039/5254* (2013.01); *C12N 2760/18222* (2013.01); *C12N 2760/18234* (2013.01); *C12N 2760/18262* (2013.01); *C12N 2760/18422* (2013.01); *C12N 2760/18434* (2013.01); *C12N 2760/18462* (2013.01)

(58) Field of Classification Search
None
See application file for complete search history.

(56) References Cited

U.S. PATENT DOCUMENTS

| 2,909,462 A | 10/1959 | Warfield et al. |
| 4,603,112 A | 7/1986 | Paoletti et al. |
| 4,722,848 A | 2/1988 | Paoletti et al. |
| 4,769,330 A | 9/1988 | Paoletti et al. |
| 5,174,993 A | 12/1992 | Paoletti |
| 5,756,103 A | 5/1998 | Paoletti et al. |
| 6,358,500 B1 | 3/2002 | Simon |
| 6,719,979 B2 | 4/2004 | Peeters et al. |
| 6,919,084 B2 | 7/2005 | Goutebroze |
| 7,371,395 B2 | 5/2008 | Parisot et al. |
| 2003/0190330 A1 | 10/2003 | Kai et al. |
| 2009/0068221 A1 | 3/2009 | Morrison |
| 2011/0052627 A1 | 3/2011 | Chaplin |
| 2013/0230529 A1 | 9/2013 | Yuen et al. |

FOREIGN PATENT DOCUMENTS

| WO | 98/16247 A1 | 4/1998 |
| WO | 2009128867 A2 | 10/2009 |

OTHER PUBLICATIONS

Krumm et al., The Measles Virus Nucleocapsid Protein Tail Domain Is Dispensable for Viral Polymerase Recruitment and Activity, 2013, Journal of biological chemistry, vol. 288, No. 41, pp. 29943-29953.*

Cheng et al., Isolation and sequence analysis of a canine distemper virus from a raccoon dog in Jilin Province, China, 2015, Virus Genes, vol. 51, pp. 298-301.*

Guillaume et al., Specific detection of Nipah virus using real-time RT-PCR (TaqMan), 2004, Journal of Virological Methods, vol. 120, pp. 229-237.*

Vaidya et al., Detection of measles, mumps and rubella viruses byimmuno-colorimetric assay and its application in focusreduction neutralization tests, 2014, Microbiology and Immunology, vol. 58, pp. 666-674.*

International Search Report and Written Opinion issued in related International Application No. PCT/US2016/062324 dated Feb. 7, 2017.

Database UniProt [Online] Oct. 1, 2000 (Oct. 1, 2000), "RecName: Full=Nucleocapsid {ECO:0000256IRuleBase:RU361245}; AltName: Full=Nucleocapsid protein {ECO:0000256I RuleBase:RU361245};", retrieved from EBI accession No. Uniprot:Q9IZC1 Database accession No. Q9IZC1 ; -& Renshaw R W et al: "Identification and Phylogenetic Comparison of Salem Virus, a Novel Paramyxovirus of Horses", Virology, Elsevier, Amsterdam, NL, vol. 270, No. 2, May 10, 2000 (May 10, 2000), pp. 417-429, XP004436312, ISSN: 0042-6822, DOI: 10.1006/VIRO.2000.0305; -& Anderson DE et al: "Genome characterization of Salem virus reveals its evolutionary intermediate status in the subfamily", Archives of Virology; Official Journal of the Virology Divisionof the International Union of Microbiological Societies, Springer-Verlag, VI, vol. 157, No. 10, Jun. 23, 2012 (Jun. 23, 2012), pp. 1989-1993, XP035117960, ISSN: 1432-8798, DOI: 10.1007/S00705-012-1388-6.

(Continued)

*Primary Examiner* — Benjamin P Blumel
(74) *Attorney, Agent, or Firm* — Meunier Carlin & Curfman LLC

(57) ABSTRACT

Disclosed herein is a strategy for the engineering of recombinant vaccines against major human and animal pathogens of the paramyxovirus family. Also disclosed are recombinant virus able to replicate without being pathogenic. Also disclosed is a method of immunizing a subject against infection with a that involves administering to the subject a recombinant vaccine disclosed herein.

16 Claims, 9 Drawing Sheets

Specification includes a Sequence Listing.

(56) References Cited

OTHER PUBLICATIONS

Database UniProt [Online] Jul. 22, 2015 (Jul. 22, 2015), "RecName: Full=Nucleocapsid {ECO:0000256IRuleBase:RU361245}; AltName: Full=Nucleocapsid protein {ECO:0000256I RuleBase:RU361245};", retrieved from EBI accession No. Uniprot:A0A0F7R6B0 Database accession No. A0A0F7R6B0 ; & S. Sakaguchi et al: "Genetic diversity of feline morbilliviruses isolated in Japan", Journal of General Virology., vol. 95, No. Pt_?, Apr. 11, 2014 (Apr. 11, 2014), pp. 1464-1468, XP055415460, GB ISSN: 0022-1317, DOI: 10.1099/vir.0.065029-0.
Krumm, Stephanie A. et al. "The Measles Virus Nucleocapsid Protein Trail Domain is Dispensable for Viral Polymerase Recruitment Activity." Journal of Biological Chemistry, vol. 288, No. 41, Oct. 11, 2013: 29943-29953.
Extended European Search Report issued in connection with European Application No. 16867058.6, dated Aug. 9, 2019, 10 pages.

\* cited by examiner

FIG 6A recCDV N tail amino acid sequences recCDV:
KTTEDRTKATGPKQSQTFLHERS.....EVANQQPPTINKRSEN.....QGGDKYPIHFSDERLPGYTPDVNSSEWSESRYQTQHQSDQGNDDDRKSMEAIAKMRMLTKMLSQPGTSEDNSPVYSDKELLN* recCDV NΔ 440-480:
KTTEDRTKATGPKQSQTFLHERS.....EVANQQPPTINKRSEN.....................................DGNDDDRKSMEAIAKMRMLTKMLSQPGTSEDNSPVYSDKELLN* recCDV NΔ 425-480:
KTTEDRTKATGPKQSQTFLHSERSSAQ.........................................................DGNDDDRKSMEAIAKMRMLTKMLSQPGTSEDNSPVYSDKELLN*

FIG 7A

FIG 7B clinical symptoms after primary infection

|  | Rash | Fever | Weight loss |
|---|---|---|---|
| recCDV NΔ 425-480 | ■■□□ | ■■■■ | ■■■■ |
| recCDV NΔ 440-480 | □□□□ | □■■■ | □□□□ |
| recCDV | ■■■■ | ■■■■ | ■■■■ |

FIG 8 percent survival vs days post infection

— CDV Ndelta440-480
— CDV Ndelta425-480
— recCDV

SEQUENCE LISTING

<160> NUMBER OF SEQ ID NOS: 6

<210> SEQ ID NO 1
<211> LENGTH: 523
<212> TYPE: PRT
<213> ORGANISM: canine distemper virus

<400> SEQUENCE: 1

```
Met Ala Ser Leu Leu Lys Ser Leu Thr Leu Phe Lys Arg Thr Arg Asp
1               5                   10                  15

Gln Pro Pro Leu Ala Ser Gly Ser Gly Gly Ala Ile Arg Gly Ile Lys
            20                  25                  30

His Val Ile Ile Val Leu Ile Pro Gly Asp Ser Ser Ile Val Thr Arg
        35                  40                  45

Ser Arg Leu Leu Asp Arg Leu Val Arg Leu Val Gly Asp Pro Glu Ile
    50                  55                  60

Asn Gly Pro Lys Leu Thr Gly Ile Leu Ile Ser Ile Leu Ser Leu Phe
65                  70                  75                  80

Val Glu Ser Pro Gly Gln Leu Ile Gln Arg Ile Ile Asp Asp Pro Asp
                85                  90                  95

Val Ser Ile Lys Leu Val Glu Val Ile Pro Ser Ile Asn Ser Val Cys
            100                 105                 110

Gly Leu Thr Phe Ala Ser Arg Gly Ala Ser Leu Asp Ser Glu Ala Asp
        115                 120                 125

Glu Phe Phe Lys Ile Val Asp Glu Gly Ser Lys Ala Gln Gly Gln Leu
    130                 135                 140

Gly Trp Leu Glu Asn Lys Asp Ile Val Asp Ile Glu Val Asp Asp Ala
145                 150                 155                 160

Glu Gln Phe Asn Ile Leu Leu Ala Ser Ile Leu Ala Gln Thr Trp Ile
                165                 170                 175

Leu Leu Ala Lys Ala Val Thr Ala Pro Asp Thr Ala Ala Asp Ser Glu
            180                 185                 190

Met Arg Arg Trp Ile Lys Tyr Thr Gln Gln Arg Arg Val Val Gly Glu
        195                 200                 205

Phe Arg Met Asn Lys Ile Trp Leu Asp Ile Val Arg Asn Arg Ile Ala
    210                 215                 220

Glu Asp Leu Ser Leu Arg Arg Phe Met Val Ala Leu Ile Leu Asp Ile
```

```
                    225                 230                 235                 240
Lys Arg Ser Pro Gly Asn Lys Pro Arg Ile Ala Glu Met Ile Cys Asp
                245                 250                 255

Ile Asp Asn Tyr Ile Val Glu Ala Gly Leu Ala Ser Phe Ile Leu Thr
                260                 265                 270

Ile Lys Phe Gly Ile Glu Thr Met Tyr Pro Ala Leu Gly Leu His Glu
            275                 280                 285

Phe Ser Gly Glu Leu Thr Thr Ile Glu Ser Leu Met Met Leu Tyr Gln
290                 295                 300

Gln Met Gly Glu Thr Ala Pro Tyr Met Val Ile Leu Glu Asn Ser Val
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Ala Leu Ala Ala Glu Leu
370                 375                 380

Gly Ile Thr Lys Glu Glu Ala Gln Leu Val Ser Glu Ile Ala Ser Lys
385                 390                 395                 400

Thr Thr Glu Asp Arg Thr Ile Arg Ala Ala Gly Pro Lys Gln Ser Gln
                405                 410                 415

Ile Thr Phe Leu His Ser Glu Arg Ser Glu Val Thr Asn Gln Gln Pro
            420                 425                 430

Pro Ala Ile Asn Lys Arg Ser Glu Asn Gln Gly Gly Asp Lys Tyr Pro
        435                 440                 445

Ile His Phe Ser Asp Glu Arg Phe Pro Gly Tyr Thr Pro Asp Val Asn
    450                 455                 460

Gly Ser Glu Trp Ser Glu Ser Arg Tyr Asp Thr Gln Thr Ile Gln Asp
465                 470                 475                 480

Asp Gly Asn Asp Asp Asp Arg Lys Ser Met Glu Ala Ile Ala Lys Met
                485                 490                 495

Arg Met Leu Thr Lys Met Leu Ser Gln Pro Gly Thr Ser Glu Gly Gly
            500                 505                 510

Ser Pro Val Tyr Asn Asp Arg Glu Leu Leu Asn
        515                 520

<210> SEQ ID NO 2
<211> LENGTH: 1572
<212> TYPE: DNA
<213> ORGANISM: canine distemper virus

<400> SEQUENCE: 2
atggccagcc ttcttaagag cctcacattg ttcaagagga ctcgggacca accccacttt      60
gcctcgggct ccggaggagc aataagaggg ataaagcatg tcattatagt cctaatcccg     120
ggtgattcga gcattgttac aagatctcga ctattggata gacttgttag attggtcggt     180
gatccggaaa tcaacggacc taaattaact gggattttaa tcagtatcct ctccttgttc     240
gtggagtccc ctggacagtt gatccagagg atcatagacg accctgatgt aagcatcaag     300
ttagtagagg tcatcccaag catcaactct gtttgcggtc ttacatttgc atccagagga     360
gcaagtttgg attctgaggc agatgagttc ttcaaaattg tagacgaagg gtcgaaagct     420
caaggacaat taggctggtt ggagaataag gatattgtag acatagaagt tgatgatgct     480
```

-continued

```
gagcaattca atatcttgct agcttccatc ttggctcaaa cttggatcct gctcgctaaa    540
gcagtgactg ctcctgatac tgcagccgac tcggagatga aaggtggat taagtatacc     600
caacagagac gtgtggtcgg ggaatttaga atgaacaaaa tctggcttga tattgttaga    660
aacaggattg ctgaggactt atctttgagg cggttcatgg tagcactcat cttggatatc    720
aaacgatccc cagggaacaa gcctagaatt gctgaaatga tttgtgatat agataactac    780
attgtggaag ctgattagc tagtttcatc ttaactatca aatttggcat gaaactatg      840
tatccggctc ttgggttgca tgagttttct ggagagttaa caactattga atcccttatg    900
atgctatacc aacagatggg tgaaacagca ccgtacatgg ttattctgga aaattctgtt    960
cagaacaaat ttagtgcagg atcctaccca ttgctctgga gttatgccat gggagttggt   1020
gttgaacttg aaaactccat ggagggtta aatttcggta gatcctactt tgatccagct    1080
tatttcaggc tcgggcaaga aatggtcaga agatctgccg gcaaagtgag ctctgcactt   1140
gccgccgagc ttggcatcac caaggaagag gctcagctag tgtcagaaat agcatccaag   1200
acaacggagg accggacaat tcgcgctgct ggtcccaagc aatctcaaat cacttttctg   1260
cactcagaaa gatccgaagt cactaatcaa caaccccag ccatcaacaa gaggtccgag    1320
aaccaaggag gagacaaata ccccatccac ttcagtgatg aacggtttcc ggggtatacc   1380
ccagatgtca acggctccga atggagtgaa tcacgctatg atacccaaac tattcaagat   1440
gatggaaacg acgatgacag gaaatcaatg gaagcaatcg ccaagatgag aatgcttacc   1500
aagatgctca gtcaacctgg gactagcgaa ggggttctc ccgtctataa tgatagagag    1560
ctactcaatt aa                                                       1572
```

<210> SEQ ID NO 3
<211> LENGTH: 487
<212> TYPE: PRT
<213> ORGANISM: Artificial Sequence
<220> FEATURE:
<223> OTHER INFORMATION: Synthetic Construct

<400> SEQUENCE: 3

```
Met Ala Ser Leu Leu Lys Ser Leu Thr Leu Phe Lys Arg Thr Arg Asp
1               5                   10                  15

Gln Pro Pro Leu Ala Ser Gly Ser Gly Gly Ala Ile Arg Gly Ile Lys
            20                  25                  30

His Val Ile Ile Val Leu Ile Pro Gly Asp Ser Ser Ile Val Thr Arg
        35                  40                  45

Ser Arg Leu Leu Asp Arg Leu Val Arg Leu Val Gly Asp Pro Glu Ile
    50                  55                  60

Asn Gly Pro Lys Leu Thr Gly Ile Leu Ile Ser Ile Leu Ser Leu Phe
65                  70                  75                  80

Val Glu Ser Pro Gly Gln Leu Ile Gln Arg Ile Ile Asp Asp Pro Asp
                85                  90                  95

Val Ser Ile Lys Leu Val Glu Val Ile Pro Ser Ile Asn Ser Val Cys
            100                 105                 110

Gly Leu Thr Phe Ala Ser Arg Gly Ala Ser Leu Asp Ser Glu Ala Asp
        115                 120                 125

Glu Phe Phe Lys Ile Val Asp Glu Gly Ser Lys Ala Gln Gly Gln Leu
    130                 135                 140

Gly Trp Leu Glu Asn Lys Asp Ile Val Asp Ile Glu Val Asp Asp Ala
145                 150                 155                 160
```

```
Glu Gln Phe Asn Ile Leu Leu Ala Ser Ile Leu Ala Gln Thr Trp Ile
                165                 170                 175
Leu Leu Ala Lys Ala Val Thr Ala Pro Asp Thr Ala Ala Asp Ser Glu
            180                 185                 190
Met Arg Arg Trp Ile Lys Tyr Thr Gln Gln Arg Arg Val Val Gly Glu
        195                 200                 205
Phe Arg Met Asn Lys Ile Trp Leu Asp Ile Val Arg Asn Arg Ile Ala
    210                 215                 220
Glu Asp Leu Ser Leu Arg Phe Met Val Ala Leu Ile Leu Asp Ile
225                 230                 235                 240
Lys Arg Ser Pro Gly Asn Lys Pro Arg Ile Ala Glu Met Ile Cys Asp
                245                 250                 255
Ile Asp Asn Tyr Ile Val Glu Ala Gly Leu Ala Ser Phe Ile Leu Thr
            260                 265                 270
Ile Lys Phe Gly Ile Glu Thr Met Tyr Pro Ala Leu Gly Leu His Glu
        275                 280                 285
Phe Ser Gly Glu Leu Thr Thr Ile Glu Ser Leu Met Met Leu Tyr Gln
    290                 295                 300
Gln Met Gly Glu Thr Ala Pro Tyr Met Val Ile Leu Glu Asn Ser Val
305                 310                 315                 320
Gln Asn Lys Phe Ser Ala Gly Ser Tyr Pro Leu Leu Trp Ser Tyr Ala
                325                 330                 335
Met Gly Val Gly Val Glu Leu Glu Asn Ser Met Gly Leu Asn Phe
            340                 345                 350
Gly Arg Ser Tyr Phe Asp Pro Ala Tyr Phe Arg Leu Gly Gln Glu Met
        355                 360                 365
Val Arg Arg Ser Ala Gly Lys Val Ser Ser Ala Leu Ala Ala Glu Leu
    370                 375                 380
Gly Ile Thr Lys Glu Glu Ala Gln Leu Val Ser Glu Ile Ala Ser Lys
385                 390                 395                 400
Thr Thr Glu Asp Arg Thr Ile Arg Ala Ala Gly Pro Lys Gln Ser Gln
                405                 410                 415
Ile Thr Phe Leu His Ser Glu Arg Ser Glu Val Thr Asn Gln Gln Pro
            420                 425                 430
Pro Ala Ile Asn Lys Arg Ser Glu Asn Ser Ala Gln Asp Gly Asn Asp
        435                 440                 445
Asp Asp Arg Lys Ser Met Glu Ala Ile Ala Lys Met Arg Met Leu Thr
    450                 455                 460
Lys Met Leu Ser Gln Pro Gly Thr Ser Glu Gly Gly Ser Pro Val Tyr
465                 470                 475                 480
Asn Asp Arg Glu Leu Leu Asn
                485

<210> SEQ ID NO 4
<211> LENGTH: 464
<212> TYPE: PRT
<213> ORGANISM: Artificial Sequence
<220> FEATURE:
<223> OTHER INFORMATION: Synthetic Construct

<400> SEQUENCE: 4

Met Ala Ser Leu Leu Lys Ser Leu Thr Leu Phe Lys Arg Thr Arg Asp
1               5                   10                  15
Gln Pro Pro Leu Ala Ser Gly Ser Gly Gly Ala Ile Arg Gly Ile Lys
            20                  25                  30
```

-continued

```
His Val Ile Ile Val Leu Ile Pro Gly Asp Ser Ser Ile Val Thr Arg
         35                  40                  45

Ser Arg Leu Leu Asp Arg Leu Val Arg Leu Val Gly Asp Pro Glu Ile
 50                  55                  60

Asn Gly Pro Lys Leu Thr Gly Ile Leu Ile Ser Ile Leu Ser Leu Phe
 65                  70                  75                  80

Val Glu Ser Pro Gly Gln Leu Ile Gln Arg Ile Ile Asp Asp Pro Asp
                 85                  90                  95

Val Ser Ile Lys Leu Val Glu Val Ile Pro Ser Ile Asn Ser Val Cys
             100                 105                 110

Gly Leu Thr Phe Ala Ser Arg Gly Ala Ser Leu Asp Ser Glu Ala Asp
         115                 120                 125

Glu Phe Phe Lys Ile Val Asp Glu Gly Ser Lys Ala Gln Gly Gln Leu
     130                 135                 140

Gly Trp Leu Glu Asn Lys Asp Ile Val Asp Ile Glu Val Asp Asp Ala
145                 150                 155                 160

Glu Gln Phe Asn Ile Leu Leu Ala Ser Ile Leu Ala Gln Thr Trp Ile
                 165                 170                 175

Leu Leu Ala Lys Ala Val Thr Ala Pro Asp Thr Ala Ala Asp Ser Glu
             180                 185                 190

Met Arg Arg Trp Ile Lys Tyr Thr Gln Gln Arg Arg Val Val Gly Glu
         195                 200                 205

Phe Arg Met Asn Lys Ile Trp Leu Asp Ile Val Arg Asn Arg Ile Ala
     210                 215                 220

Glu Asp Leu Ser Leu Arg Arg Phe Met Val Ala Leu Ile Leu Asp Ile
225                 230                 235                 240

Lys Arg Ser Pro Gly Asn Lys Pro Arg Ile Ala Glu Met Ile Cys Asp
                 245                 250                 255

Ile Asp Asn Tyr Ile Val Glu Ala Gly Leu Ala Ser Phe Ile Leu Thr
             260                 265                 270

Ile Lys Phe Gly Ile Glu Thr Met Tyr Pro Ala Leu Gly Leu His Glu
         275                 280                 285

Phe Ser Gly Glu Leu Thr Thr Ile Glu Ser Leu Met Met Leu Tyr Gln
     290                 295                 300

Gln Met Gly Glu Thr Ala Pro Tyr Met Val Ile Leu Glu Asn Ser Val
305                 310                 315                 320

Gln Asn Lys Phe Ser Ala Gly Ser Tyr Pro Leu Leu Trp Ser Tyr Ala
                 325                 330                 335

Met Gly Val Gly Val Glu Leu Glu Asn Ser Met Gly Gly Leu Asn Phe
             340                 345                 350

Gly Arg Ser Tyr Phe Asp Pro Ala Tyr Phe Arg Leu Gly Gln Glu Met
         355                 360                 365

Val Arg Arg Ser Ala Gly Lys Val Ser Ser Ala Leu Ala Ala Glu Leu
     370                 375                 380

Gly Ile Thr Lys Glu Glu Ala Gln Leu Val Ser Glu Ile Ala Ser Lys
385                 390                 395                 400

Thr Thr Glu Asp Arg Thr Ile Arg Ala Ala Gly Pro Lys Gln Ser Gln
                 405                 410                 415

Ile Thr Ser Ala Gln Asp Gly Asn Asp Asp Arg Lys Ser Met Glu
             420                 425                 430

Ala Ile Ala Lys Met Arg Met Leu Thr Lys Met Leu Ser Gln Pro Gly
         435                 440                 445

Thr Ser Glu Gly Gly Ser Pro Val Tyr Asn Asp Arg Glu Leu Leu Asn
```

<210> SEQ ID NO 5
<211> LENGTH: 1464
<212> TYPE: DNA
<213> ORGANISM: Artificial Sequence
<220> FEATURE:
<223> OTHER INFORMATION: Synthetic Construct

<400> SEQUENCE: 5

```
atggccagcc ttcttaagag cctcacattg ttcaagagga ctcgggacca accccccactt    60
gcctcgggct ccggaggagc aataagaggg ataaagcatg tcattatagt cctaatcccg   120
ggtgattcga gcattgttac aagatctcga ctattggata gacttgttag attggtcggt   180
gatccggaaa tcaacggacc taaattaact gggattttaa tcagtatcct ctccttgttc   240
gtggagtccc ctggacagtt gatccagagg atcatagacg accctgatgt aagcatcaag   300
ttagtagagg tcatcccaag catcaactct gtttgcggtc ttacatttgc atccagagga   360
gcaagtttgg attctgaggc agatgagttc ttcaaaattg tagacgaagg tcgaaagct   420
caaggacaat taggctggtt ggagaataag gatattgtag acatagaagt tgatgatgct   480
gagcaattca atatcttgct agcttccatc ttggctcaaa cttggatcct gctcgctaaa   540
gcagtgactg ctcctgatac tgcagccgac tcggagatga aaggtggat taagtatacc   600
caacagagac gtgtggtcgg ggaatttaga atgaacaaaa tctggcttga tattgttaga   660
aacaggattg ctgaggactt atctttgagg cggttcatgg tagcactcat cttggatatc   720
aaacgatccc cagggaacaa gcctagaatt gctgaaatga tttgtgatat agataactac   780
attgtggaag ctggattagc tagtttcatc ttaactatca aatttggcat tgaaactatg   840
tatccggctc ttgggttgca tgagttttct ggagagttaa caactattga atcccttatg   900
atgctatacc aacagatggg tgaaacagca ccgtacatgg ttattctgga aaattctgtt   960
cagaacaaat ttagtgcagg atcctaccca ttgctctgga gttatgccat gggagttggt  1020
gttgaacttg aaaactccat gggagggtta aatttcggta gatcctactt tgatccagct  1080
tatttcaggc tcgggcaaga aatggtcaga agatctgccg gcaaagtgag ctctgcactt  1140
gccgccgagc ttggcatcac caaggaagag gctcagctag tgtcagaaat agcatccaag  1200
acaacggagg accggacaat tcgcgctgct ggtcccaagc aatctcaaat cactttttctg  1260
cactcagaaa gatccgaagt cactaatcaa caaccccccag ccatcaacaa gaggtccgag  1320
aacagcgctc aagatggaaa cgacgatgac aggaaatcaa tggaagcaat cgccaagatg  1380
agaatgctta ccaagatgct cagtcaacct gggactagcg aagggggttc tcccgtctat  1440
aatgatagag agctactcaa ttaa                                        1464
```

<210> SEQ ID NO 6
<211> LENGTH: 1395
<212> TYPE: DNA
<213> ORGANISM: Artificial Sequence
<220> FEATURE:
<223> OTHER INFORMATION: Synthetic Construct

<400> SEQUENCE: 6

```
atggccagcc ttcttaagag cctcacattg ttcaagagga ctcgggacca accccccactt    60
gcctcgggct ccggaggagc aataagaggg ataaagcatg tcattatagt cctaatcccg   120
ggtgattcga gcattgttac aagatctcga ctattggata gacttgttag attggtcggt   180
gatccggaaa tcaacggacc taaattaact gggattttaa tcagtatcct ctccttgttc   240
```

-continued

```
gtggagtccc ctggacagtt gatccagagg atcatagacg accctgatgt aagcatcaag        300
ttagtagagg tcatcccaag catcaactct gtttgcggtc ttacatttgc atccagagga        360
gcaagtttgg attctgaggc agatgagttc ttcaaaattg tagacgaagg gtcgaaagct        420
caaggacaat taggctggtt ggagaataag gatattgtag acatagaagt tgatgatgct        480
gagcaattca atatcttgct agcttccatc ttggctcaaa cttggatcct gctcgctaaa        540
gcagtgactg ctcctgatac tgcagccgac tcggagatga gaaggtggat taagtatacc        600
caacagagac gtgtggtcgg ggaatttaga atgaacaaaa tctggcttga tattgttaga        660
aacaggattg ctgaggactt atctttgagg cggttcatgg tagcactcat cttggatatc        720
aaacgatccc cagggaacaa gcctagaatt gctgaaatga tttgtgatat agataactac        780
attgtggaag ctggattagc tagtttcatc ttaactatca aatttggcat tgaaactatg        840
tatccggctc ttgggttgca tgagttttct ggagagttaa caactattga atcccttatg        900
atgctatacc aacagatggg tgaaacagca ccgtacatgg ttattctgga aaattctgtt        960
cagaacaaat ttagtgcagg atcctaccca ttgctctgga gttatgccat gggagttggt       1020
gttgaacttg aaaactccat gggagggtta aatttcggta gatcctactt tgatccagct       1080
tatttcaggc tcgggcaaga aatggtcaga agatctgccg gcaaagtgag ctctgcactt       1140
gccgccgagc ttggcatcac caaggaagag gctcagctag tgtcagaaat agcatccaag       1200
acaacggagg accggacaat tcgcgctgct ggtcccaagc aatctcaaat cactagcgct       1260
caagatggaa acgacgatga caggaaatca atggaagcaa tcgccaagat gagaatgctt       1320
accaagatgc tcagtcaacc tgggactagc gaagggggtt ctcccgtcta taatgataga       1380
gagctactca attaa                                                         1395
```

TUNABLE VACCINE PLATFORM AGAINST PATHOGENS OF THE PARAMYXOVIRUS FAMILY

CROSS-REFERENCE TO RELATED APPLICATIONS

This application is a national stage application filed under 35 U.S.C. § 371 of PCT/US2016/062324 filed Nov. 16, 2016, which claims benefit of U.S. Provisional Application No. 62/255,711, filed Nov. 16, 2015, each of which are hereby incorporated herein by reference in their entirety.

BACKGROUND

Canine distemper is one of the most serious viral diseases of dogs. The disease is highly contagious and is characterized by severe morbidity and high mortality. Modified live canine distemper virus (CDV) vaccines are currently available in the United States. They do provide protective immunity to distemper, but such vaccines may revert to virulence, may cause immunosuppression following vaccination, and have been shown to cause mortality in non-canine species. CDV belongs to the genus *Morbillivirus* of the family Paramyxoviridae. First-generation recombinant paramyxovirus vaccines propagate efficiently in cell culture, but do not provide full protection against a subsequent lethal challenge with wild type virus. There is therefore an urgent need for the design of a next-generation recombinant paramyxovirus vaccine that interfaces the induction of robust immunity with superior vaccine safety.

SUMMARY

Disclosed herein is a strategy for the engineering of recombinant vaccines against major pathogens of the paramyxovirus family, such as CDV of the *Morbillivirus* genus and highly pathogenic zoonotic members of the *Henipavirus* genus. This strategy is based on the discovery of a region within the viral nucleoprotein, a structural protein that encapsidates the viral genome, that is essential for viral pathogenesis but dispensable for virus replication. Therefore, also disclosed are recombinant non-pathogenic paramyxovirus vaccines produced using mutant nucleoproteins carrying deletions that allows the paramyxovirus virus to replicate efficiently in cell culture but lack pathogenicity in vivo. In some cases, the deletions are 40 to 60 amino acids in length. Since a large section of the nucleoprotein is deleted from the vaccine and paramyxoviruses of different strains do not recombine their genomes after co-infection, this vaccine engineering strategy excludes reversion of the engineered vaccine strain to pathogenic wild type virus by design.

In some embodiments, the disclosed recombinant non-pathogenic paramyxovirus vaccine comprises a paramyxovirus genome encoding an infectious paramyxovirus virion operably linked to an expression control sequence. In these embodiments, the paramyxovirus genome comprises a nucleic acid encoding a nucleoprotein having a deletion that allows a paramyxovirus virus produced by expression of the paramyxovirus vector to replicate without being pathogenic.

The disclosed attenuation strategy can also be combined with an exchange of the envelope glycoprotein currently present in the construct with that of newly emerging strains. Since the glycoproteins are immunodominant, this strategy can be used to update the vaccine with the glycoproteins of newly emerging strains that will ensure optimal protection against future challenges.

The family Paramyxoviridae is composed of a diverse group of viruses and is divided into two subfamilies, Paramyxovirinae and Pneumovirinae. There are currently 40 virus species classified within the Paramyxovirinae subfamily, but several remain unclassified at the genus level. In the past few decades, paramyxoviruses have been discovered from terrestrial, volant and aquatic animals, demonstrating a vast host range and great viral genetic diversity.

In some embodiments, the paramyxovirus comprises a *morbillivirus*, such as a canine distemper virus (CDV) or a peste-des-petits-ruminants virus (PPRV). In some cases, the paramyxovirus comprises an *avulavirus, aquaparamyxovirus, henipavirus, respirovirus, rubulavirus*, or *ferlavirus*. For example, the paramyxovirus can be a nipah virus, hendra virus, parainfluenza viruses type I-IV, or mumps virus.

In some embodiments, the region in the viral nucleoprotein that is essential for viral pathogenesis but dispensable for virus replication corresponds to residues 442-480 of SEQ ID NO:1. In some embodiments, the region in the viral nucleoprotein that is essential for viral pathogenesis but dispensable for virus replication corresponds approximately to residues 421-480 or 428-480 of SEQ ID NO:1. In some cases, the size of the deletion affects the amount of attenuation. Therefore, smaller and larger deletions are contemplated for use in the disclosed compositions and methods to adjust viral attenuation in the vaccine product to optimal levels.

Therefore, disclose is a paramyxovirus nucleoprotein having a deletion that corresponds to residues 442-480 of SEQ ID NO:1, or at least 10, 15, 16, 17, 18, 19, 20, 21, 22, 23, 24, 25, 26, 27, 28, 29, 30, 31, 32, 33, 34, 35, 36, or 37 of these residues. In some cases, the deletion that corresponds to residues 440-480 of SEQ ID NO:1. In some cases, the deletion that corresponds to residues 421-480 of SEQ ID NO:1. In some cases, the deletion is at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 residues that corresponds to residues 421-480 of SEQ ID NO:1. In some cases, the deletion corresponds to residues 428-480 of SEQ ID NO:1.

Also disclosed is a recombinant nucleic acid, comprising a paramyxovirus nucleoprotein having a mutation or deletion that allows a paramyxovirus virus produced by expression of the paramyxovirus vector to replicate without being pathogenic, operably linked to a heterologous expression control sequence.

Also disclosed is a paramyxovirus vector comprising the disclosed recombinant nucleic acid encoding a mutant paramyxovirus nucleoprotein. Also disclosed is an infectious paramyxovirus virion produced by expression of the disclosed recombinant paramyxovirus vector in a host cell.

Also disclosed is a method of immunizing a subject against infection with a paramyxovirus that involves administering to the subject a recombinant vaccine disclosed herein. For example, the vaccine can be administered by intramuscular or intradermal injection. In addition, the method can further involve administering to the subject an adjuvant, which can be administered separately, or can be contained within a composition with the recombinant vaccine composition.

The details of one or more embodiments of the invention are set forth in the accompanying drawings and the descrip-

DESCRIPTION OF DRAWINGS

Figures 1, 2:
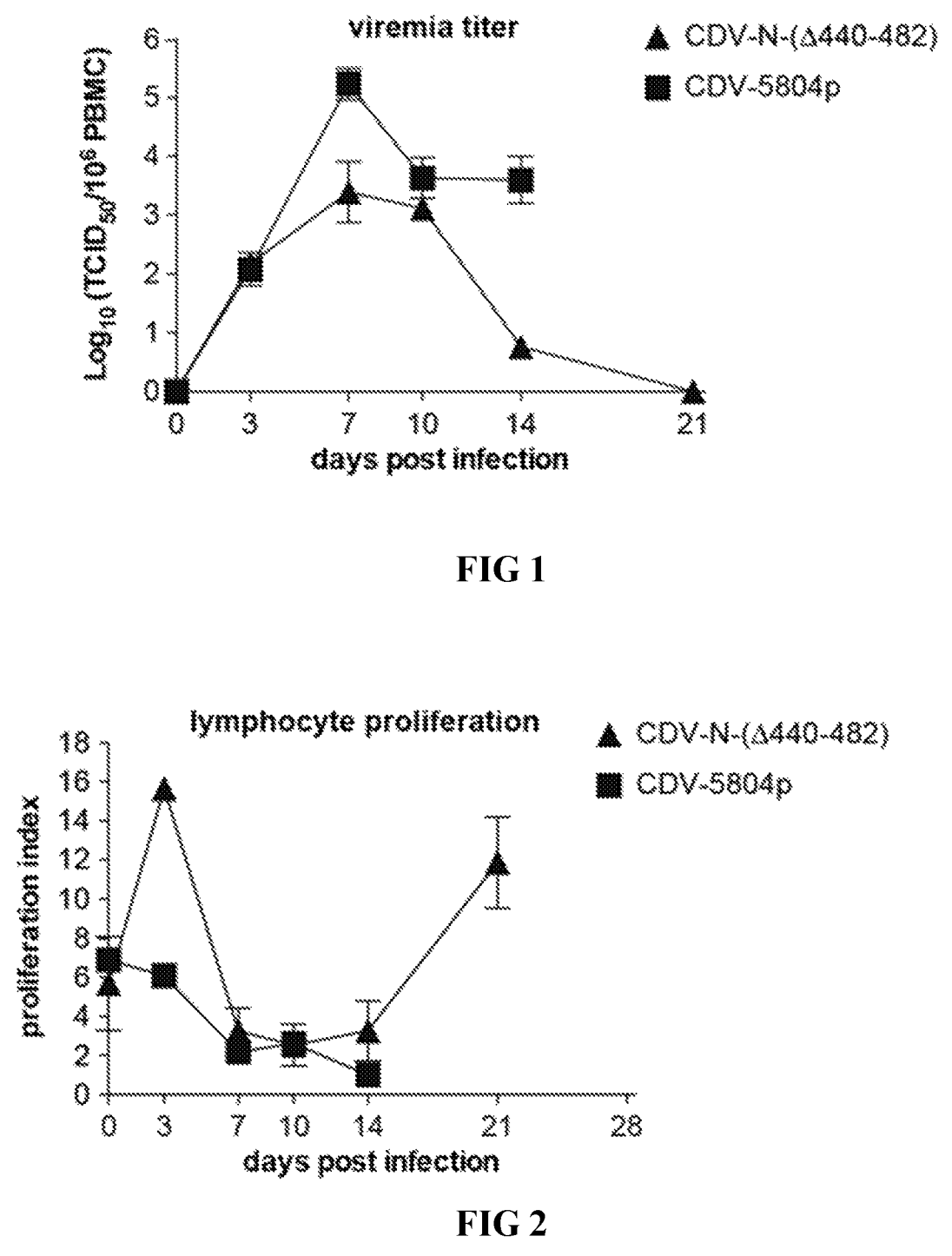

FIG. 1 is a graph showing viremia titer ($Log_{10}$ ($TCID_{50}$/$10^6$ PBMC) of pathogenic recombinant CDV-5804p (■) and recombinant CDV-N-(Δ440-482) (▲) derived from CDV-5804p as a function of time (days) post-infection.

FIG. 2 is a graph showing lymphocyte proliferation (proliferation index) as a function of time (days) post-infection with CDV-5804p (■) and CDV-N-(Δ440-482) (▲).

Figures 3, 4:
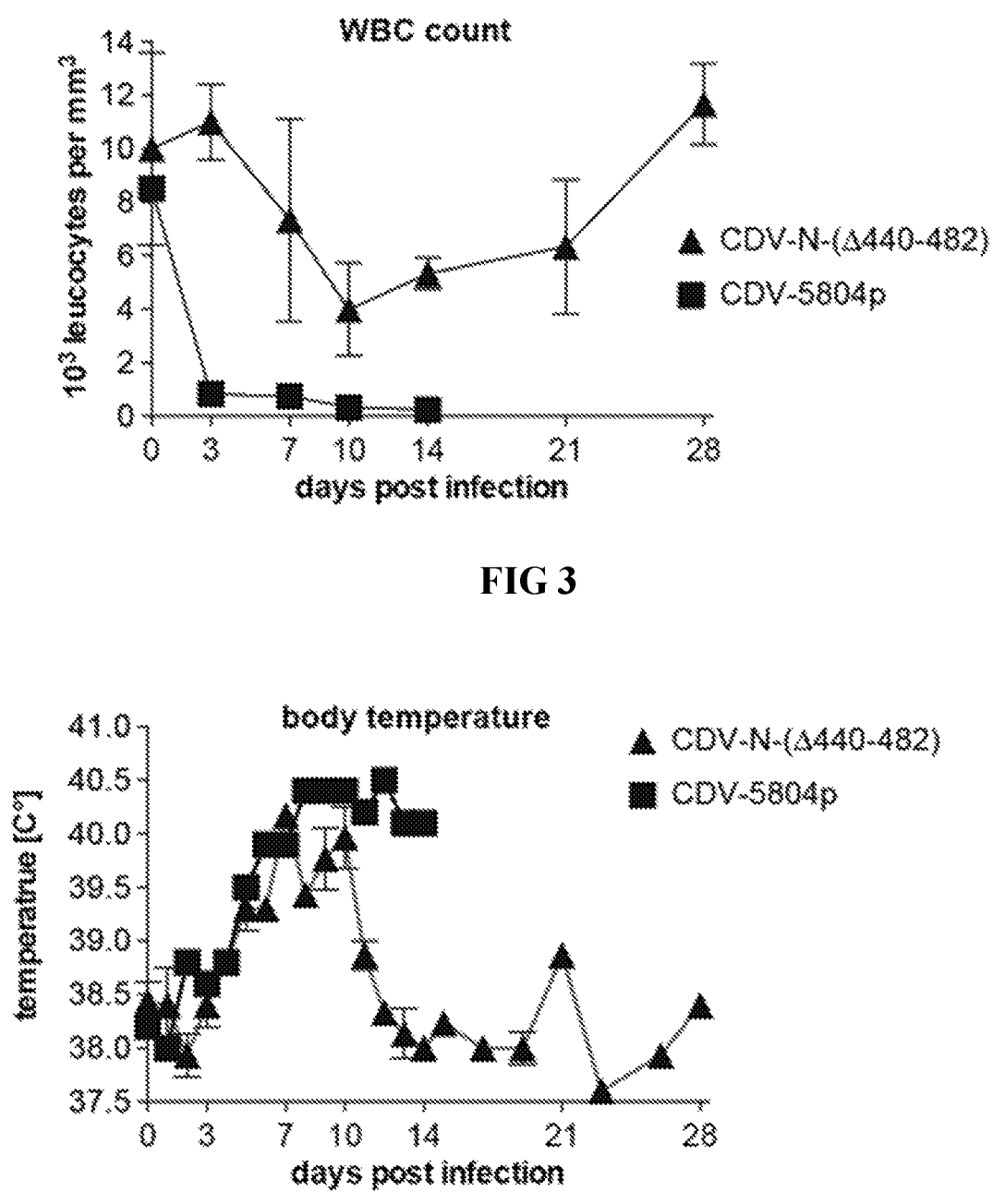

FIG. 3 is a graph showing white blood cell count ($10^3$ leucocytes per $mm^3$) as a function of time (days) post-infection with CDV-5804p (■) and CDV-N-(Δ440-482) (▲)

FIG. 4 is a graph showing body temperature (C.°) as a function of time (days) post-infection with CDV-5804p (■) and CDV-N-(Δ440-482) (▲)

Figures 5, 6A:
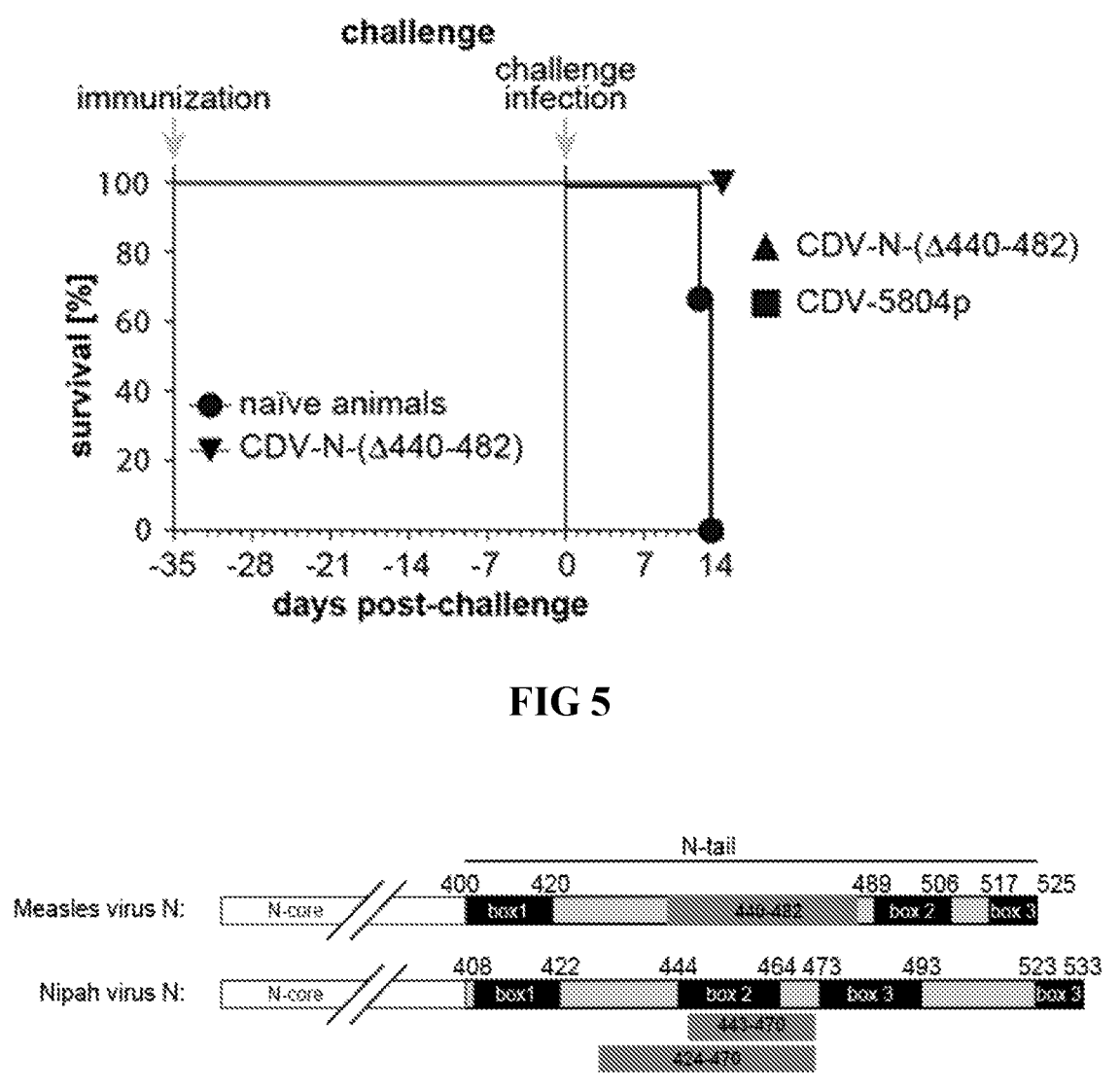

FIG. 5 is a graph showing survival (%) of naïve animals (●) and CDV-N-(Δ440-482) immunized animals (▼) as a function of time (days post challenge). Immunization occurred 35 days prior to challenge infection.

FIG. 6A illustrates the gene structure of the N-tail of measles virus and Nipah virus (NiV) N protein.

FIG. 7A shows the N-tail amino acid sequence of recombinant CDV (recCDV), CDV-N-(Δ440-480), and CDV-N-(Δ4250-480). FIG. 7B is a graph showing virus titer ($TCID_{50}$/ml) as a function of time (hrs) post-infection for recCDV (diamond), CDV-N-(Δ440-480) (square), and CDV-N-(Δ4250-480) (triangle).

FIG. 8 illustrates clinical symptoms after primary infection with recCDV, CDV-N-(Δ440-480), and CDV-N-(Δ4250-480).

FIG. 9 is a graph showing percent survival as a function of days post infection with recCDV, CDV-N-(Δ440-480), and CDV-N-(Δ4250-480).

FIG. 11A is a graph showing percent survival as a function of days post infection with mock vaccination, CDV-N-(Δ440-480), and CDV-N-(Δ4250-480) challenged with lethal dose at day 49. FIG. 11B illustrates clinical symptoms after lethal infection with mock vaccination, CDV-N-(Δ440-480), and CDV-N-(Δ4250-480).

DETAILED DESCRIPTION

Figure 6B:
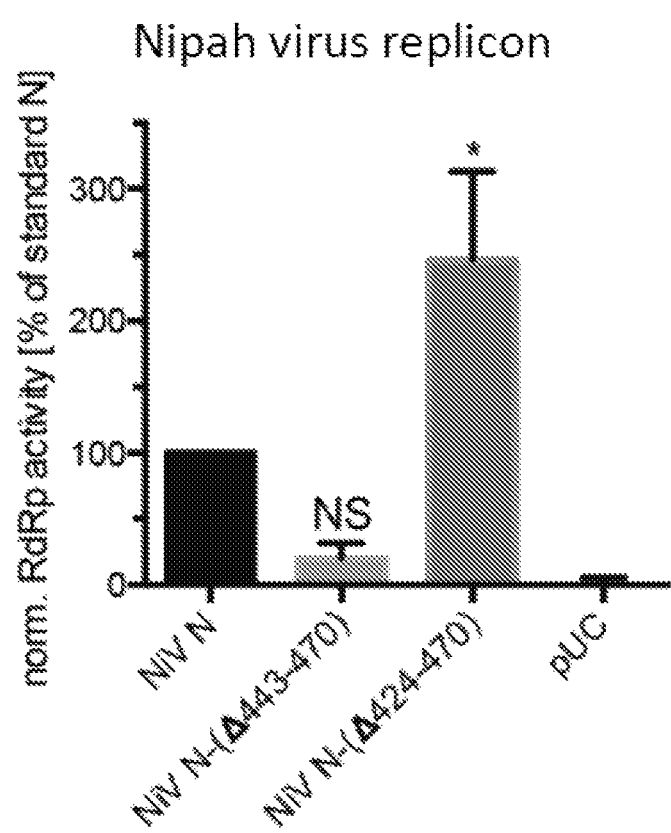
FIG. 6B is a bar graph showing RdRp activity (% of standard) for NiV N, NiV N (Δ443-470), NiV N (Δ424-470), and pUC.

The disclosed compositions and methods relate to a vaccine or composition comprising (i) a recombinant paramyxovirus and (ii) a pharmaceutically acceptable carrier. Also disclosed are methods for modifying the genome of a paramyxovirus to produce recombinant paramyxoviruses or paramyxovirus viral vectors; modified paramyxoviruses prepared by such methods; DNA and protein sequences; and methods for infecting cells and host animals with such recombinant paramyxoviruses to provoke the amplification of exogenous RNA and proteins encoded by the exogenous RNA, including antigenic proteins, by said cells and host animals.

Also disclosed is a pharmaceutical composition or vaccine for inducing an immunological response in a host animal inoculated with the composition or vaccine, the composition or vaccine including a pharmaceutical acceptable carrier and a modified recombinant paramyxovirus viral vector.

Also disclosed are methods for inducing an immunological response in a subject to paramyxovirus infection, which method comprises inoculating the subject with a vaccine or a pharmaceutical composition containing the disclosed recombinant paramyxovirus vector.

The term "attenuated" refers to an organism, such as a virus, with a weakened ability to cause disease.

The term "non-pathogenic" refers to an organism, such as a virus, that does not cause disease in a healthy subject.

The term "subject" refers to any individual who is the target of administration or treatment. The subject can be a vertebrate, for example, a mammal. The subject may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), porcine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "subject" also includes an individual animal in all stages of development, including embryonic and fetal stages. The subject can be a human or veterinary patient. The term "patient" refers to a subject under the treatment of a clinician, e.g., physician.

The terms "polypeptide" and "protein" are used interchangeably herein to refer to a polymer of consecutive amino acid residues.

The terms "nucleic acid", "nucleotide", and "polynucleotide" are used interchangeably and refer to RNA, DNA, cDNA (complementary DNA), or cRNA (complementary RNA) and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5') of a cDNA copy of the single strand viral RNA genome. Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) and other cellular organelles (e.g., mitochondria). The genomic DNA or genome contemplated in the present invention also refers to the RNA of a virus. The RNA may be a positive strand or a negative strand RNA. The term "genomic DNA" includes the genomic DNA containing sequences complementary to those described herein. The term "genomic DNA" also refers to messenger RNA (mRNA), complementary DNA (cDNA), and complementary RNA (cRNA). The term "genomic RA (nucleic acid)" as used herein includes RNA, mRNA, cRNA, DNA and cDNA.

The term "heterologous DNA" as used herein refers to the DNA derived from a different organism, such as a different cell type or a different species from the recipient.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a viral vector). The choice of introducing vectors or polynucleotides will often depend on features of the host cell.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

A "vector" refers to a recombinant DNA plasmid, bacteriophage, or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector may be able to but does not need to be capable of replication in the ultimate target cell or subject. The term includes vectors for cloning as well as viral vectors.

The term "engineered" or "recombinant" means a polynucleotide of semisynthetic, or synthetic origin that either does not occur in nature or is linked to another polynucleotide in an arrangement not found in nature.

Recombinant Paramyxovirus

Disclosed herein are recombinant non-pathogenic paramyxovirus nucleic acid constructs, proteins, viruses, vectors, and virions. The virus family Paramyxoviridae includes both human (e.g. measles, mumps, Nipah, Hendra, parainfluenza and respiratory syncytial virus) and animal pathogens (e.g. canine distemper virus) that cause significant impact on public health as well as the global economy. Members of this virus family are defined by having a monopartite, negative sense, single-stranded RNA genome. The Paramyxoviridae family consists of two subfamilies namely Paramyxovirinae and Pneumovirinae. Owing to recent reclassification, the subfamily Paramyxovirinae includes five genera, i.e *Morbillivirus, Henipavirus, Rubulavirus, Respirovirus* and *Avulavirus* while Pneumovirinae includes *Pneumovirus* and *Metapneumovirus*.

Mutant Nucleoprotein

The disclosed paramyxovirus nucleic acid constructs, proteins, viruses, vectors, and virions contain a mutant paramyxovirus nucleoprotein having an internal deletion of a multiple amino acid region that allows a paramyxovirus virus with this nucleoprotein to replicate without being pathogenic.

The disclosed attenuation strategy can also be combined with an exchange of the envelope glycoprotein currently present in the construct with that of newly emerging strains. Since the glycoproteins are immunodominant, this strategy can be used to update the vaccine with the glycoproteins of newly emerging strains that will ensure optimal protection against future challenges.

In some cases, the paramyxovirus nucleoprotein is derived from CDV. A wildtype CDV nucleoprotein is provided below:

(SEQ ID NO: 1)
MASLLKSLTLFKRTRDQPPLASGSGGAIRGIKHVIIVLIPGDSSIVTRS

RLLDRLVRLVGDPEINGPKLTGILISILSLFVESPGQLIQRIIDDPDVS

IKLVEVIPSINSVCGLTFASRGASLDSEADEFFKIVDEGSKAQGQLGWL

ENKDIVDIEVDDAEQFNILLASILAQTWILLAKAVTAPDTAADSEMRRW

IKYTQQRRVVGEFRMNKIWLDIVRNRIAEDLSLRRFMVALILDIKRSPG

NKPRIAEMICDIDNYIVEAGLASFILTIKFGIETMYPALGLHEFSGELT

TIESLMMLYQQMGETAPYMVILENSVQNKFSAGSYPLLWSYAMGVGVEL

ENSMGGLNFGRSYFDPAYFRLGQEMVRRSAGKVSSALAAELGITKEEAQ

LVSETASKTTEDRTIRAAGPKQSQITFLHSERSEVTNQQPPAINKRSEN

QGGDKYPIHFSDERFPGYTPDVNGSEWSESRYDTQTIQDDGNDDDRKSM

EAIAKMRMLTKMLSQPGTSEGGSPVYNDRELLN.

A nucleic acid sequence encoding this wildtype CDV nucleoprotein is provided below:

(SEQ ID NO: 2)
ATGGCCAGCCTTCTTAAGAGCCTCACATTGTTCAAGAGGACTCGGGACC

AACCCCCACTTGCCTCGGGCTCCGGAGGAGCAATAAGAGGGATAAAGCA

TGTCATTATAGTCCTAATCCCGGGTGATTCGAGCATTGTTACAAGATCT

CGACTATTGGATAGACTTGTTAGATTGGTCGGTGATCCGGAAATCAACG

GACCTAAATTAACTGGGATTTTAATCAGTATCCTCTCCTTGTTCGTGGA

GTCCCCTGGACAGTTGATCCAGAGGATCATAGACGACCCTGATGTAAGC

ATCAAGTTAGTAGAGGTCATCCCAAGCATCAACTCTGTTTGCGGTCTTA

CATTTGCATCCAGAGGAGCAAGTTTGGATTCTGAGGCAGATGAGTTCTT

CAAAATTGTAGACGAAGGGTCGAAAGCTCAAGGACAATTAGGCTGGTTG

GAGAATAAGGATATTGTAGACATAGAAGTTGATGATGCTGAGCAATTCA

ATATCTTGCTAGCTTCCATCTTGGCTCAAACTTGGATCCTGCTCGCTAA

AGCAGTGACTGCTCCTGATACTGCAGCCGACTCGGAGATGAGAAGGTGG

ATTAAGTATACCCAACAGAGACGTGTGGTCGGGGAATTTAGAATGAACA

AAATCTGGCTTGATATTGTTAGAAACAGGATTGCTGAGGACTTATCTTT

GAGGCGGTTCATGGTAGCACTCATCTTGGATATCAAACGATCCCCAGGG

AACAAGCCTAGAATTGCTGAAATGATTTGTGATATAGATAACTACATTG

TGGAAGCTGGATTAGCTAGTTTCATCTTAACTATCAAATTTGGCATTGA

AACTATGTATCCGGCTCTTGGGTTGCATGAGTTTTCTGGAGAGTTAACA

-continued

ACTATTGAATCCCTTATGATGCTATACCAACAGATGGGTGAAACAGCAC

CGTACATGGTTATTCTGGAAAATTCTGTTCAGAACAAATTTAGTGCAGG

ATCCTACCCATTGCTCTGGAGTTATGCCATGGGAGTTGGTGTTGAACTT

GAAAACTCCATGGGAGGGTTAAATTTCGGTAGATCCTACTTTGATCCAG

CTTATTTCAGGCTCGGGCAAGAAATGGTCAGAAGATCTGCCGGCAAAGT

GAGCTCTGCACTTGCCGCCGAGCTTGGCATCACCAAGGAAGAGGCTCAG

CTAGTGTCAGAAATAGCATCCAAGACAACGGAGGACCGGACAATTCGCG

CTGCTGGTCCCAAGCAATCTCAAATCACTTTTCTGCACTCAGAAAGATC

CGAAGTCACTAATCAACAACCCCCAGCCATCAACAAGAGGTCCGAGAAC

CAAGGAGGAGACAAATACCCCATCCACTTCAGTGATGAACGGTTTCCGG

GGTATACCCCAGATGTCAACGGCTCCGAATGGAGTGAATCACGCTATGA

TACCCAAACTATTCAAGATGATGGAAACGACGATGACAGGAAATCAATG

GAAGCAATCGCCAAGATGAGAATGCTTACCAAGATGCTCAGTCAACCTG

GGACTAGCGAAGGGGGTTCTCCCGTCTATAATGATAGAGAGCTACTCAA

TTAA.

Therefore, disclosed is a paramyxovirus nucleoprotein having a deletion that corresponds to residues 442-480 of SEQ ID NO:1, or at least 10, 15, 16, 17, 18, 19, 20, 21, 22, 23, 24, 25, 26, 27, 28, 29, 30, 31, 32, 33, 34, 35, 36, or 37 of these residues. In some cases, the deletion that corresponds to residues 440-480 of SEQ ID NO:1. In some cases, the deletion that corresponds to residues 421-480 of SEQ ID NO:1. In some cases, the deletion that corresponds to residues 425-480 of SEQ ID NO:1. In some cases, the deletion is at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 residues that corresponds to residues 421-480 of SEQ ID NO:1. In some cases, the deletion is at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 residues that corresponds to residues 428-480 of SEQ ID NO:1

For example, a mutant CDV nucleoprotein lacking amino acids 442-480 is provided below:

(SEQ ID NO: 3)
MASLLKSLTLFKRTRDQPPLASGSGGAIRGIKHVIIVLIPGDSSIVTRS

RLLDRLVRLVGDPEINGPKLTGILISILSLFVESPGQLIQRIIDDPDVS

IKLVEVIPSINSVCGLTFASRGASLDSEADEFFKIVDEGSKAQGQLGWL

ENKDIVDIEVDDAEQFNILLASILAQTWILLAKAVTAPDTAADSEMRRW

IKYTQQRRVVGEFRMNKIWLDIVRNRIAEDLSLRRFMVALILDIKRSPG

NKPRIAEMICDIDNYIVEAGLASFILTIKFGIETMYPALGLHEFSGELT

TIESLMMLYQQMGETAPYMVILENSVQNKFSAGSYPLLWSYAMGVGVEL

ENSMGGLNFGRSYFDPAYFRLGQEMVRRSAGKVSSALAAELGITKEEAQ

LVSEIASKTTEDRTIRAAGPKQSQITFLHSERSEVTNQQPPAINKRSEN

SAQDGNDDDRKSMEATAKMRMLTKMLSQPGTSEGGSPVYNDRELLN.

A mutant CDV nucleoprotein lacking amino acids 421-480 is provided below:

(SEQ ID NO: 4)
MASLLKSLTLFKRTRDQPPLASGSGGAIRGIKHVIIVLIPGDSSIVTRS

RLLDRLVRLVGDPEINGPKLTGILISILSLFVESPGQLIQRIIDDPDVS

IKLVEVIPSINSVCGLTFASRGASLDSEADEFFKIVDEGSKAQGQLGWL

ENKDIVDIEVDDAEQFNILLASILAQTWILLAKAVTAPDTAADSEMRRW

IKYTQQRRVVGEFRMNKIWLDIVRNRIAEDLSLRRFMVALILDIKRSPG

NKPRIAEMICDIDNYIVEAGLASFILTIKFGIETMYPALGLHEFSGELT

TIESLMMLYQQMGETAPYMVILENSVQNKFSAGSYPLLWSYAMGVGVEL

ENSMGGLNFGRSYFDPAYFRLGQEMVRRSAGKVSSALAAELGITKEEAQ

LVSETASKTTEDRTIRAAGPKQSQITSAQDGNDDDRKSMEAIAKMRMLT

KMLSQPGTSEGGSPVYNDRELLN.

Also disclosed is a nucleic acid encoding a paramyxovirus nucleoprotein disclosed herein. Therefore, disclosed is a nucleic acid encoding a paramyxovirus nucleoprotein having a deletion that corresponds to nucleotides 1326-1440 of SEQ ID NO:2, or at least 30, 40, 50, 60, 70, 80, 90, 100, 110, 114 of these nucleotides. Also disclosed is a nucleic acid encoding a paramyxovirus nucleoprotein having a deletion that corresponds to nucleotides 1263-1440 of SEQ ID NO:2, or at least 30, 40, 50, 60, 70, 80, 90, 100, 110, 120, 130, 140, 150, 160, 170, 177 of these nucleotides.

For example, a nucleic acid sequence encoding a mutant CDV nucleoprotein lacking amino acids 442-480 is provided below:

(SEQ ID NO: 5)
ATGGCCAGCCTTCTTAAGAGCCTCACATTGTTCAAGAGGACTCGGGACC

AACCCCCACTTGCCTCGGGCTCCGGAGGAGCAATAAGAGGGATAAAGCA

TGTCATTATAGTCCTAATCCCGGGTGATTCGAGCATTGTTACAAGATCT

CGACTATTGGATAGACTTGTTAGATTGGTCGGTGATCCGGAAATCAACG

GACCTAAATTAACTGGGATTTTAATCAGTATCCTCTCCTTGTTCGTGGA

GTCCCCTGGACAGTTGATCCAGAGGATCATAGACGACCCTGATGTAAGC

ATCAAGTTAGTAGAGGTCATCCCAAGCATCAACTCTGTTTGCGGTCTTA

CATTTGCATCCAGAGGAGCAAGTTTGGATTCTGAGGCAGATGAGTTCTT

CAAAATTGTAGACGAAGGGTCGAAAGCTCAAGGACAATTAGGCTGGTTG

GAGAATAAGGATATTGTAGACATAGAAGTTGATGATGCTGAGCAATTCA

ATATCTTGCTAGCTTCCATCTTGGCTCAAACTTGGATCCTGCTCGCTAA

AGCAGTGACTGCTCCTGATACTGCAGCCGACTCGGAGATGAGAAGGTGG

ATTAAGTATACCCAACAGAGACGTGTGGTCGGGGAATTTAGAATGAACA

AAATCTGGCTTGATATTGTTAGAAACAGGATTGCTGAGGACTTATCTTT

GAGGCGGTTCATGGTAGCACTCATCTTGGATATCAAACGATCCCCAGGG

AACAAGCCTAGAATTGCTGAAATGATTTGTGATATAGATAACTACATTG

TGGAAGCTGGATTAGCTAGTTTCATCTTAACTATCAAATTTGGCATTGA

AACTATGTATCCGGCTCTTGGGTTGCATGAGTTTTCTGGAGAGTTAACA

ACTATTGAATCCCTTATGATGCTATACCAACAGATGGGTGAAACAGCAC

-continued

CGTACATGGTTATTCTGGAAAATTCTGTTCAGAACAAATTTAGTGCAGG

ATCCTACCCATTGCTCTGGAGTTATGCCATGGGAGTTGGTGTTGAACTT

GAAAACTCCATGGGAGGGTTAAATTTCGGTAGATCCTACTTTGATCCAG

CTTATTTCAGGCTCGGGCAAGAAATGGTCAGAAGATCTGCCGGCAAAGT

GAGCTCTGCACTTGCCGCCGAGCTTGGCATCACCAAGGAAGAGGCTCAG

CTAGTGTCAGAAATAGCATCCAAGACAACGGAGGACCGGACAATTCGCG

CTGCTGGTCCCAAGCAATCTCAAATCACTTTTCTGCACTCAGAAAGATC

CGAAGTCACTAATCAACAACCCCCAGCCATCAACAAGAGGTCCGAGAAC agcgctCAAGATGGAAACGACGATGACAGGAAATCAATGGAAGCAATCG

CCAAGATGAGAATGCTTACCAAGATGCTCAGTCAACCTGGGACTAGCGA

AGGGGGTTCTCCCGTCTATAATGATAGAGAGCTACTCAATTAA.

A nucleic acid sequence encoding a mutant CDV nucleoprotein lacking amino acids 421-480 is provided below:

(SEQ ID NO: 6)
ATGGCCAGCCTTCTTAAGAGCCTCACATTGTTCAAGAGGACTCGGGACC

AACCCCCACTTGCCTCGGGCTCCGGAGGAGCAATAAGAGGGATAAAGCA

TGTCATTATAGTCCTAATCCCGGGTGATTCGAGCATTGTTACAAGATCT

CGACTATTGGATAGACTTGTTAGATTGGTCGGTGATCCGGAAATCAACG

GACCTAAATTAACTGGGATTTTAATCAGTATCCTCTCCTTGTTCGTGGA

GTCCCCTGGACAGTTGATCCAGAGGATCATAGACGACCCTGATGTAAGC

ATCAAGTTAGTAGAGGTCATCCCAAGCATCAACTCTGTTTGCGGTCTTA

CATTTGCATCCAGAGGAGCAAGTTTGGATTCTGAGGCAGATGAGTTCTT

CAAAATTGTAGACGAAGGGTCGAAAGCTCAAGGACAATTAGGCTGGTTG

GAGAATAAGGATATTGTAGACATAGAAGTTGATGATGCTGAGCAATTCA

ATATCTTGCTAGCTTCCATCTTGGCTCAAACTTGGATCCTGCTCGCTAA

AGCAGTGACTGCTCCTGATACTGCAGCCGACTCGGAGATGAGAAGGTGG

ATTAAGTATACCCAACAGAGACGTGTGGTCGGGGAATTTAGAATGAACA

AAATCTGGCTTGATATTGTTAGAAACAGGATTGCTGAGGACTTATCTTT

GAGGCGGTTCATGGTAGCACTCATCTTGGATATCAAACGATCCCCAGGG

AACAAGCCTAGAATTGCTGAAATGATTTGTGATATAGATAACTACATTG

TGGAAGCTGGATTAGCTAGTTTCATCTTAACTATCAAATTTGGCATTGA

AACTATGTATCCGGCTCTTGGGTTGCATGAGTTTTCTGGAGAGTTAACA

ACTATTGAATCCCTTATGATGCTATACCAACAGATGGGTGAAACAGCAC

CGTACATGGTTATTCTGGAAAATTCTGTTCAGAACAAATTTAGTGCAGG

ATCCTACCCATTGCTCTGGAGTTATGCCATGGGAGTTGGTGTTGAACTT

GAAAACTCCATGGGAGGGTTAAATTTCGGTAGATCCTACTTTGATCCAG

CTTATTTCAGGCTCGGGCAAGAAATGGTCAGAAGATCTGCCGGCAAAGT

GAGCTCTGCACTTGCCGCCGAGCTTGGCATCACCAAGGAAGAGGCTCAG

CTAGTGTCAGAAATAGCATCCAAGACAACGGAGGACCGGACAATTCGCG

CTGCTGGTCCCAAGCAATCTCAAATCACTagcgctCAAGATGGAAACGA

CGATGACAGGAAATCAATGGAAGCAATCGCCAAGATGAGAATGCTTACC

AAGATGCTCAGTCAACCTGGGACTAGCGAAGGGGGTTCTCCCGTCTATA

ATGATAGAGAGCTACTCAATTAA.

Also disclosed are variants of the disclosed mutant nucleoproteins. Variants include homologous polypeptides having an amino acid sequence at least 75%, 80%, 85%, 90%, 95%, 96%, 97%, 98%, or 99% identity to the amino acid sequences as set forth herein.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

Also disclosed is a recombinant paramyxovirus vector comprising the disclosed recombinant nucleic acid encoding a mutant paramyxovirus nucleoprotein. Recombinant vectors may include plasmids and viral vectors and may be used for in vitro or in vivo expression. Recombinant vectors may also include a signal peptide. Signal peptides are short peptide chain (3-60 amino acids long) that direct the post-translational transport of a protein (which are synthesized in the cytosol) to certain organelles such as the nucleus, mitochondrial matrix, endoplasmic reticulum, chloroplast, apoplast and peroxisome. The signal peptide may be cleaved off rapidly upon translation. The signal sequence may be the natural sequence or a peptide signal from a secreted protein e.g. the signal peptide from the tissue plasminogen activator protein (tPA), or the signal peptide from insulin-like growth factor 1 (IGF1). Upon translation, the unprocessed polypeptide may be cleaved at a cleavage site to lead to the mature polypeptide.

A plasmid may include a DNA transcription unit, for instance a nucleic acid sequence that permits it to replicate in a host cell, such as an origin of replication (prokaryotic or eukaryotic). A plasmid may also include one or more selectable marker genes and other genetic elements known in the art. Circular and linear forms of plasmids are encompassed in the present disclosure.

Also disclosed is an in vivo expression vector comprising a polynucleotide sequence, which contains and expresses in vivo in a host the disclosed paramyxovirus polypeptides and/or variants or fragments thereof. The in vivo expression vector may include any transcription unit containing a polynucleotide or a gene of interest and those essential elements for its in vivo expression. These expression vectors may be plasmids or recombinant viral vectors. For in vivo expression, the promoter may be of viral or cellular origin. In one embodiment, the promoter may be the bacteriophage T7-polymerase promoter, the human RNA polymerase I (PolI) promoter, the cytomegalovirus (CMV) early promoter (CMV-IE promoter), the SV40 virus early or late promoter or the Rous Sarcoma virus LTR promoter, a promoter of a cytoskeleton gene, such as the desmin promoter, or the actin promoter. When several genes are present in the same plasmid, they may be provided in the same transcription unit or in different units.

As used herein, the term "plasmid" may include any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention. The plasmids may also comprise other transcription-regulating elements such as, for example, stabilizing sequences of the intron type.

Construction of recombinant virus is well known in the art as described in, e.g., U.S. Pat. Nos. 4,769,330, 4,722,848, 4,603,112, 5,174,993, and 5,756,103, 6,719,979.

Also disclosed are methods for the administration of a therapeutically effective amount of a paramyxovirus vaccine disclosed herein. Determination of the therapeutically effective amount is routine experimentation for one of ordinary skill in the art. In one embodiment, the paramyxovirus vaccine formulation comprises an expression vector comprising a polynucleotide that encodes the disclosed recombinant paramyxovirus and a pharmaceutically or veterinarily acceptable carrier, vehicle or excipient. In another embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro), or facilitating transfection and/or improve preservation of the vector (or protein). Doses and dose volumes are herein discussed in the general description and can also be determined by the skilled artisan from this disclosure read in conjunction with the knowledge in the art, without any undue experimentation.

In another embodiment, pharmaceutically or veterinarily acceptable carrier, excipient, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, from 3 to 8 p/v %, the latter being in total or in part, or in a mixture either polyglycerol esters, said polyglycerol esters being polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (see, e.g., U.S. Pat. No. 6,358,500). Examples of other suitable emulsions are described in U.S. Pat. No. 7,371,395.

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121. Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

Also disclosed is a method for inducing an immunological response in an animal to an antigen, which method comprises inoculating the animal with a paramyxovirus vaccine disclosed herein. In some embodiments, the method involves a prime-boost administration regimen, which is comprised of at least one primary administration and at least one booster administration. The immunological composition or vaccine used in primary administration may be same, may be different in nature from those used as a booster. The primary administration may comprise one or more administrations of the same viral vector-based immunological compositions of vaccines. Similarly, the booster administration may comprise one or more administrations of the same viral vector-based or immunological composition of vaccine. The administration route of the prime and the boost may be the same or different. Similarly, the origin of the protective gene present in the prime and the boost may be the same or different (e.g. different strain). The various administrations are preferably carried out 1 to 6 weeks apart, and more particularly about 3 weeks apart. According to a preferred mode, an annual booster, preferably using the viral vector-based immunological composition of vaccine, is also envisaged. The subjects are preferably at least one day old at the time of the first administration.

A variety of administration routes may be used such as subcutaneously or intramuscularly, intradermally, transdermally, spray, drinking water, eye drop, intranasal, oral, oral baits, in ovo or a combination (e.g. oculonasal, oronasal). This administration may be made by a syringe with a needle, microneedle, or with a needle free apparatus like Dermojet or Biojector (Bioject, Oregon, USA) or Vetjet™ (Merial) or Vitajet™ (Bioject Inc.). The dosage may be from about $10^3$ pfu to about $10^9$ pfu per recombinant paramyxovirus vector. The volume of doses may be from about 0.01 ml to 0.2 ml, and is advantageously 0.1 ml. Administration may comprise multiple points of injection.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Pathogenesis Study of Mutant Nucleoprotein in a Ferret Model

FIGS. 1 to 5 show pathogenesis study results and protective effect of a recombinant CDV harboring a mutant nucleoprotein (CDV-N-(Δ440-482)) in comparison to standard recombinant CDV (CDV-5804p) in a ferret model.

Example 2: Expansion of Engineered Paramyxovirus Attenuation Through Partial Nucleocapsid (N) Protein Tail Truncation for Vaccine Strain Design to the *Henipavirus* Genus Signature paramyxoviruses of the *henipavirus* genus are highly pathogenic and recognized as potential bioterrorism threats. Despite a case fatality rate approaching 70% in some outbreaks, no vaccine or therapeutic strategy is currently approved for human use. Towards expanding the strategy of engineered paramyxovirus attenuation through partial N protein tail truncation for vaccine strain design, proof-of-concept was established for the feasibility of the approach to the Nipah virus (NiV) polymerase complex, the signature pathogen of the *henipavirus* genus and primary clinical threat. Since NiV is a select agent requiring BSL-4 biocontainment, these pilot experiments were carried out using a plasmid-based NIV-derived minigenome reporter system that allows monitoring of NIV RNA-dependent RNA-polymerase (RdRp) complex activity under BSL-2 biosafety conditions. Having identified a suitable area for partial NiV N protein tail truncation based on experience with the related measles virus (MeV) and canine distemper virus (CDV) systems (FIG. 6A), candidate N tail truncated NiV N protein expression plasmids were generated. Applied to the NiV minireplicon system, some of these modified N proteins maintained bioactivity similar or exceeding that of standard NiV N (FIG. 6B).

These findings resemble previous results obtained for tail truncated MeV and CDV N proteins in the corresponding MeV and CDV minireplicon systems, and therefore support the overall feasibility of engineering attenuated NiV recombinants strains that lack a central section of the structurally disordered N tail domain and provide a suitable platform for a live-attenuated NiV vaccine.

Example 3: Altering the Length of the N Tail Truncations Modulates the Degree of Virus Attenuation In Vivo, Providing a Mechanism to Optimize Vaccine Efficacy and Safety Through Fine Tuning Fitness and Residual Pathogenesis of the Vaccine Candidate Strain It is a groundbreaking advantage of the disclosed strategy towards engineered paramyxovirus attenuation that the approach was designed to provide a mechanism to balance the degree of vaccine stain attenuation vs. residual viral pathogenesis. Being able to fine tuning these parameters has the potential to be game-changing for CDV and NiV vaccine design, since over-attenuation compromises vaccine efficacy while under-attenuation may results in unacceptable vaccine safety profiles. Both issues have, for instance, considerable hampered efforts towards vaccine development against a related respiratory pathogen, respiratory syncytial virus, over the past five decades.

Figure 10:
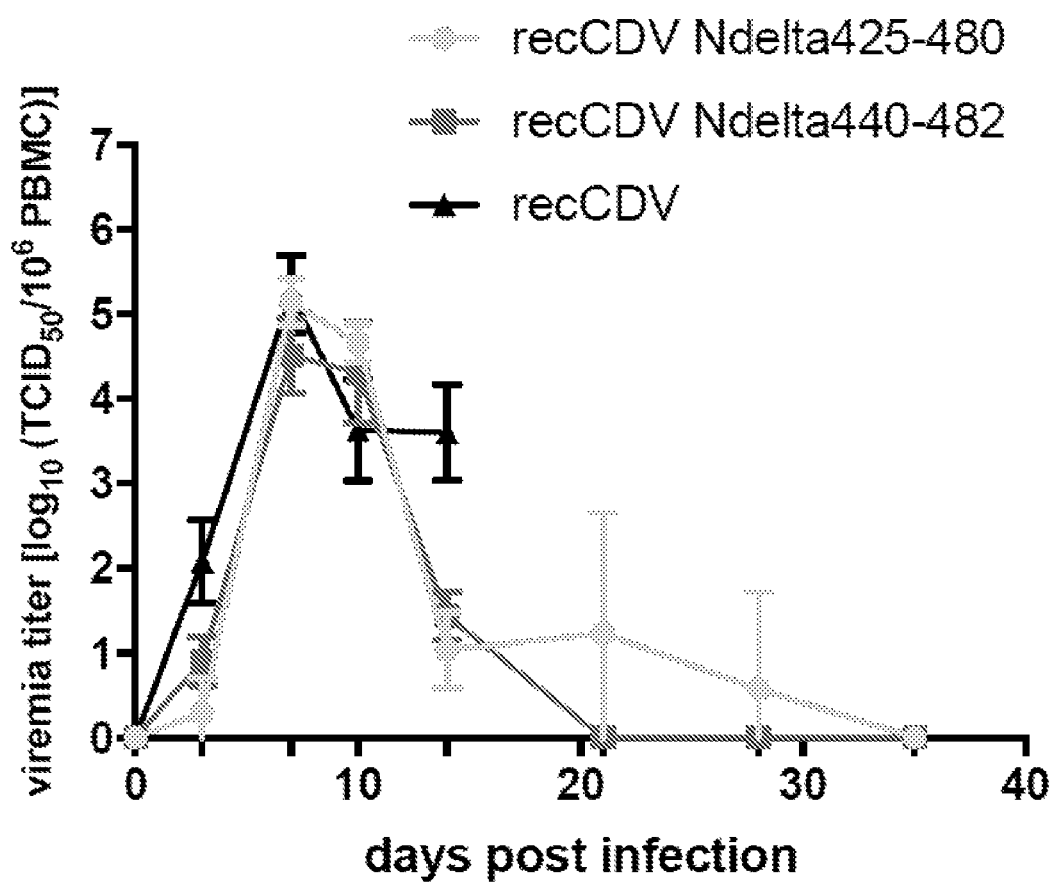
FIG. 10 is a graph showing viremia titer (log 10 ($TCID_{50}$/$10^6$ PBMC)) as a function of days post-infection with recCDV, CDV-N-(Δ440-480), and CDV-N-(Δ4250-480).
Figures 11A, 11B:
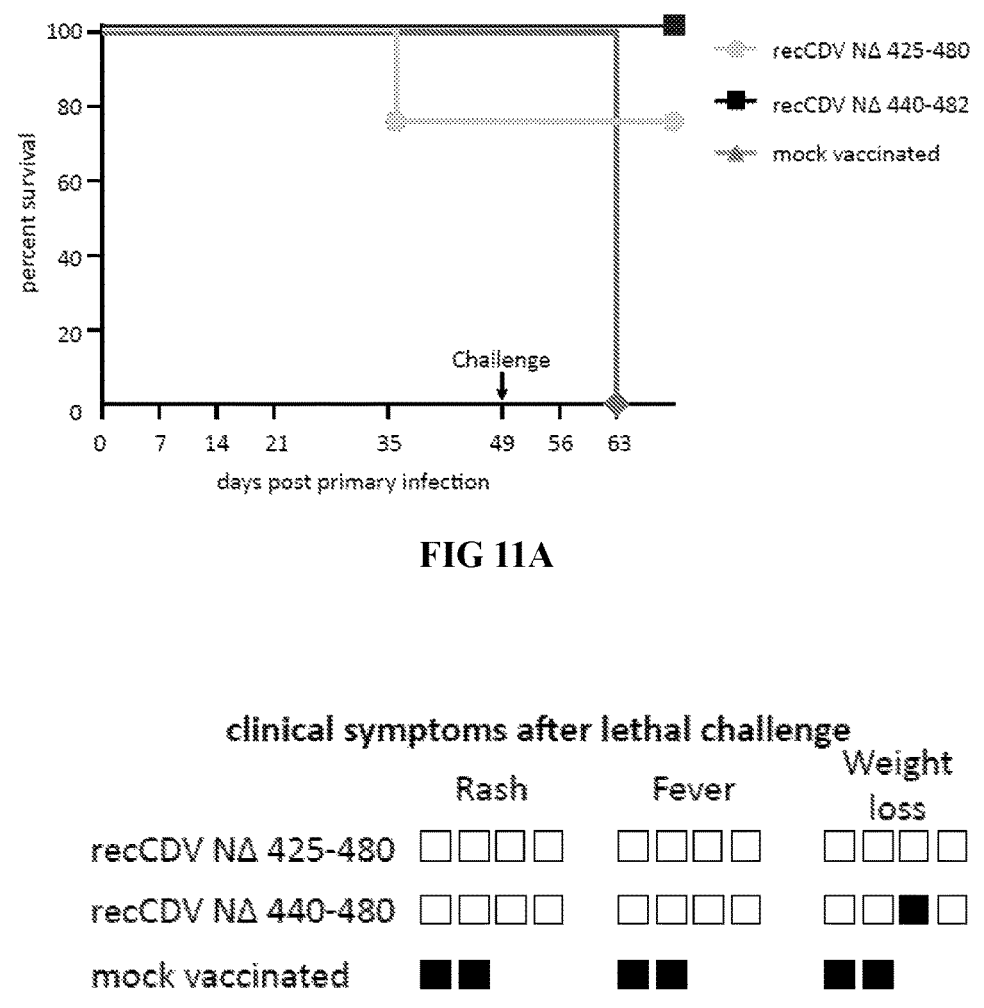

To conceptually test this key feature of the disclosed paramyxovirus attenuation approach through partial N protein tail truncations, a new CDV recombinant with expanded internal N tail truncation was generated and recovered; this strain lacked N protein tail residues 426-479, as compared to the original proof-of-concept CDV strain harboring an N tail truncation spanning from residues 441-479 (FIG. 7A). Both strains grew efficiently in cell culture (FIG. 7B). When both strains were subjected to pathogenesis testing in the ferret animal model, original results obtained for the recCDV-NΔ440-480 strain were fully reproduced: this recombinant was strongly attenuated, all recipient animals survived infection with minimal symptoms, cell-associated peak viremia titers were slightly reduced compared to the unmodified parental recombinant strain (FIGS. 8, 9, and 10). By comparison, the newly generated recCDV-NΔ425-480 strain was only partially attenuated, reflected by appreciable disease symptoms in all infected animals (FIG. 8), only 75% survival of animals of this cohort (FIG. 9), and higher peak viremia titers compared to the recCDV-NΔ440-480 candidate (FIG. 10). Importantly, surviving animals vaccinated with either mutant strain were fully protected against a subsequent challenge with a lethal dose of pathogenic CDV (FIG. 11).

These results demonstrate that virus recombinants with different length internal N protein tail truncations are viable and grow efficiently in cell culture, but differ in their level of attenuation vs. residual pathogenesis in vivo. While a direct proportionality between truncation length and degree of attenuation is lacking, the disclosed results illuminate a groundbreaking new mechanism to dial engineered paramyxovirus attenuation to the optimal level for maximal vaccine efficacy by varying the length of the structurally disordered central N tail domain. Combined with our observation that even extended viral passaging (>10 consecutive passages followed by RT-PCR and DNA sequencing) does not result in the emergence of RdRp mutations restoring viral fitness, these findings spotlight the N tail truncation approach as a powerful innovative strategy for the development of much needed next-generation paramyxovirus vaccines.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

What is claimed is:

1. A recombinant non-pathogenic paramyxovirus vaccine, comprising a paramyxovirus genome encoding an infectious paramyxovirus virion operably linked to an expression control sequence, wherein the paramyxovirus genome comprises a nucleic acid encoding a nucleoprotein having a deletion that allows a paramyxovirus virus produced by expression of the paramyxovirus vector to replicate without being pathogenic, wherein the deletion corresponds to residues 442-480 of SEQ ID NO:1.

2. The recombinant vaccine of claim 1, wherein the paramyxovirus comprises a *morbillivirus*.

3. The recombinant vaccine of claim 2, wherein the paramyxovirus comprises a canine distemper virus (CDV).

4. The recombinant vaccine of claim 2, wherein the paramyxovirus comprises a measles virus or Peste-des-petits-ruminants (PPRV).

5. The recombinant vaccine of claim 1, wherein the paramyxovirus comprises a *avulavirus*, aquaparamyxovirus, *henipavirus*, respirovirus, rubulavirus, or *ferlavirus*.

6. The recombinant vaccine of claim 5, wherein the paramyxovirus comprises a nipah virus or hendra virus.

7. The recombinant vaccine of claim 5, wherein the paramyxovirus comprises a human parainfluenzaviruses type I-IV or mumps virus.

8. The recombinant vaccine of claim 1, wherein the nucleoprotein comprises a deletion that corresponds to residues 440-480 of SEQ ID NO:1.

9. The recombinant vaccine of claim 1, wherein the nucleoprotein comprises a deletion that corresponds to residues 421-480 of SEQ ID NO:1.

10. An infectious paramyxovirus virion produced by expression of the recombinant paramyxovirus vector of claim 1 in a host cell.

11. A recombinant nucleic acid, comprising a paramyxovirus nucleoprotein having a deletion that allows a paramyxovirus virus produced by expression of the paramyxovirus vector to replicate without being pathogenic, operably linked to a heterologous expression control sequence, wherein the deletion corresponds to residues 442-480 of SEQ ID NO: 1.

12. The recombinant nucleic acid of claim 11, wherein the nucleoprotein comprises a deletion that corresponds to residues 440-480 of SEQ ID NO:1.

13. The recombinant nucleic acid of claim 11, wherein the nucleoprotein comprises a deletion that corresponds to residues 421-480 of SEQ ID NO:1.

14. A method of immunizing a subject against infection with a paramyxovirus, comprising administering to the subject the recombinant vaccine of claim 1.

15. The method of claim 14, wherein administering comprises intramuscular or intradermal injection.

16. The method of claim 14, further comprising administering to the subject an adjuvant.

* * * * *